US012337055B2

(12) United States Patent
Bauer et al.

(10) Patent No.: US 12,337,055 B2
(45) Date of Patent: Jun. 24, 2025

(54) BLEACHING COMPOSITION FOR KERATIN FIBERS

(71) Applicant: KAO CORPORATION, Tokyo (JP)

(72) Inventors: Peter Bauer, Darmstadt (DE); Steven Breakspear, Darmstadt (DE); Bernd Nöcker, Darmstadt (DE); Ines Rabelo De Moraes, Darmstadt (DE)

(73) Assignee: KAO CORPORATION, Tokyo (JP)

( * ) Notice: Subject to any disclaimer, the term of this patent is extended or adjusted under 35 U.S.C. 154(b) by 101 days.

(21) Appl. No.: 17/652,516

(22) Filed: Feb. 25, 2022

(65) Prior Publication Data

US 2022/0273542 A1 Sep. 1, 2022

(30) Foreign Application Priority Data

Feb. 26, 2021 (EP) .................................... 21159626

(51) Int. Cl.

| | |
|---|---|
| ***A61K 8/60*** | (2006.01) |
| ***A61K 8/22*** | (2006.01) |
| ***A61K 8/25*** | (2006.01) |
| ***A61K 8/34*** | (2006.01) |
| ***A61K 8/44*** | (2006.01) |
| ***A61K 8/46*** | (2006.01) |
| ***A61K 8/73*** | (2006.01) |
| ***A61Q 5/02*** | (2006.01) |
| ***A61Q 5/08*** | (2006.01) |
| ***A61Q 5/12*** | (2006.01) |

(52) U.S. Cl.

CPC .................. *A61K 8/60* (2013.01); *A61K 8/22* (2013.01); *A61K 8/25* (2013.01); *A61K 8/342* (2013.01); *A61K 8/44* (2013.01); *A61K 8/463* (2013.01); *A61K 8/731* (2013.01); *A61Q 5/02* (2013.01); *A61Q 5/08* (2013.01); *A61Q 5/12* (2013.01); *A61K 2800/4324* (2013.01); *A61K 2800/882* (2013.01); *A61K 2800/884* (2013.01)

(58) Field of Classification Search

CPC ........................................................ A61K 8/60

See application file for complete search history.

(56) References Cited

U.S. PATENT DOCUMENTS

| | | | |
|---|---|---|---|
| 4,900,545 | A | 2/1990 | Wisotzki et al. |
| 7,815,900 | B1 | 10/2010 | Cannell et al. |
| 2005/0058618 | A1 | 3/2005 | Evans et al. |
| 2007/0226916 | A1 | 10/2007 | Mellul et al. |
| 2010/0055060 | A1 | 3/2010 | Yoshida et al. |
| 2017/0360670 | A1 | 12/2017 | Pratt et al. |

FOREIGN PATENT DOCUMENTS

| | | | | |
|---|---|---|---|---|
| DE | 102005062646 | A1 * | 6/2007 | ............... A61K 8/42 |
| DE | 10 2017 211 645 | A1 | 1/2019 | |
| EP | 0 525 239 | A1 | 2/1993 | |
| EP | 1 842 528 | A1 | 10/2007 | |
| EP | 3 040 065 | A1 | 7/2016 | |
| EP | 2 608 848 | B1 | 4/2017 | |
| EP | 3453380 | A1 * | 3/2019 | |
| WO | WO 02/03937 | A2 | 1/2002 | |
| WO | WO-2016142269 | A1 * | 9/2016 | ............ A61K 8/342 |

OTHER PUBLICATIONS

Translated DE 102005062646 A1 (Year: 2007).* https://foodb.ca/compounds/FDB000756 (Year: 2023).*

Translated WO 2016/142269 A1 (Year: 2016).*

Extended European Search Report issued Sep. 15, 2021 in European Application 21159626.7 filed on Feb. 26, 2021, 14 pages (with Written Opinion).

Hollenberg et al., "Möglichkeiten zur Verbesserung der Haarstruktur mit kosmetischen Mittel", Seifen, Oele, Fette, Wachse, Augsburg, DE, vol. 117, No. 1, Jan. 1, 1991, 5 pages.

"Hair Bleaching Agent", Database GNPD [Online] Mintel , Oct. 5, 2020, 6 pages, Database accession No. 8158129.

"Diva Hair Color", Database GNPD [Online] Mintel , Oct. 20, 1999, 3 pages, Database accession No. 10062789.

"Shampoo", Database GNPD [Online] Mintel , Jan. 29, 2021, 3 pages, Database accession No. 8451149.

"Shampoo-Conditioner" , Database GNPD [Online] Mintel , Sep. 24, 2020, 3 pages, Database accession No. 8133663.

"Hydrating Shampoo", Database GNPD [Online] Mintel , Jan. 14, 2021, 3 pages, Database accession No. 8406667.

* cited by examiner

*Primary Examiner* — Andrew S Rosenthal
*Assistant Examiner* — Danielle Kim
(74) *Attorney, Agent, or Firm* — Oblon, McClelland, Maier & Neustadt, L.L.P.

(57) ABSTRACT

The present invention is directed to a kit-of-parts for bleaching keratin fibers, comprising: an aqueous composition A comprising a) one or more non-acetylated sugar alcohol(s), and/or their mixtures, a bleaching composition B comprising b) one or more persalt(s) and/or peroxy salt(s), c) one or more alkalizing agent(s), and an aqueous oxidizing composition C, wherein the total concentration of compound(s) according to a) in the aqueous composition A is in the range of 1% to 50% by weight, calculated to the total weight of the aqueous composition A, and wherein the bleaching composition B comprises less than 5% by weight of water, calculated to the total weight of the bleaching composition B.

15 Claims, No Drawings

BLEACHING COMPOSITION FOR KERATIN FIBERS

CROSS REFERENCES TO RELATED APPLICATIONS

This application claims priority to European Patent Application No. 21159626.7, filed on Feb. 26, 2021, which is incorporated herein by reference in its entirety.

FIELD OF THE INVENTION

The invention is directed to the provision of a bleaching and dyeing method for keratin fibers.

BACKGROUND OF THE INVENTION

Many consumers are unsatisfied with their hair color. Changes of hair color, in most cases, require the lightening of hair, especially for dark hair customers. A common technique is hair bleaching of whole hair as well partial treatments such as streaks. For such treatments a high degree of lightening is desired.

One way to increase lightening performance of bleaching compositions is the use of a reductive pre-treatment step, e.g., by using organic thiols (EP2608848) or inorganic reducing agents such as sulfites. However, with a reductive pre-treatment step hair lightening and hair damage are increased simultaneously.

EP0525239 discloses the use of acetylated sugar alcohols at concentrations of 45% by weight or more to increase the performance of perborate bleach for textile fibers.

EP3040065 discloses the use of mono- and disaccharides in aqueous oxidizing composition.

Thus, there is a real need to develop bleaching composition, which deliver an increased degree of lightening without leading to high degrees of damage.

SUMMARY OF THE INVENTION

Therefore, the first object of the present invention is a kit-of-parts for bleaching keratin fibers, preferably human keratin fibers, more preferably human hair, comprising:

an aqueous composition A comprising a) one or more non-acetylated sugar alcohol(s), and/or their mixtures, a bleaching composition B comprising b) one or more persalt(s) and/or peroxy salt(s), c) one or more alkalizing agent(s), an aqueous oxidizing composition C, wherein the total concentration of compound(s) according to a) in the aqueous composition A is in the range of 1% to 50% by weight, calculated to the total weight of the aqueous composition A, and wherein the bleaching composition B comprises less than 5% by weight of water, calculated to the total weight of the bleaching composition B.

The second object of the present invention is a method for bleaching of keratin fibers, preferably human keratin fibers, more preferably human hair, comprising the steps in the following order:

i) applying to keratin fibers an aqueous composition A as defined above, ii) leaving the keratin fibers for a time period in the range of 1 min to 48 h, iii) optionally rinsing-off and optionally drying the keratin fibers, iv) mixing a bleaching composition B with an aqueous oxidizing composition C to yield a ready-to-use composition having a pH in the range of 7 to 12, v) applying the ready-to-use composition onto keratin fibers and leaving it for a time period in the range of 1 min to 60 min, vi) rinsing-off the keratin fibers.

The third object of the present invention is a use of an aqueous composition A as defined above as pre-treatment composition for bleaching of keratin fibers, preferably of human keratin fibers, more preferably of human hair.

DETAILED DESCRIPTION OF THE INVENTION

Inventors of the present invention have unexpectedly found out that the objects of the present invention increase bleaching performance while not leading to elevated damage of keratin fibers. Moreover, due to the mildness of the compositions to fibers, they feel more cosmetic, healthier, and appear to have more shine.

Kit-Of-Parts

The present invention is directed to a kit-of-parts for bleaching keratin fibers, preferably human keratin fibers, more preferably human hair, comprising:

an aqueous composition A comprising a) one or more non-acetylated sugar alcohol(s), and/or their mixtures, a bleaching composition B comprising b) one or more persalt(s) and/or peroxy salt(s), c) one or more alkalizing agent(s), an aqueous oxidizing composition C, wherein the total concentration of compound(s) according to a) in the aqueous composition A is in the range of 1% to 50% by weight, calculated to the total weight of the aqueous composition A, and wherein the bleaching composition B comprises less than 5% by weight of water, calculated to the total weight of the bleaching composition B.

Aqueous Composition A

The aqueous composition A comprises non-acetylated sugar alcohol(s), and/or their mixtures, as compound(s) according to group a).

It is further preferred from the viewpoint of bleaching power that the one or more non-acetylated sugar alcohol(s) as compound(s) according to group a) is/are mannitol, sorbitol, xylitol, and/or their mixtures, most preferably it is mannitol.

It is further preferred from the viewpoint of bleaching power that the total concentration of compound(s) according to a) is 0.5% by weight or more, preferably 1% by weight or more, more preferably 2% by weight or more, further more preferably 3% by weight or more, still further more preferably 5% by weight or more, calculated to the total weight of the aqueous composition A.

It is further preferred from the viewpoint of bleaching power and composition viscosity that the total concentration of compound(s) according to a) is 30% by weight or less, more preferably 25% by weight or less, still more preferably 20% by weight or less, further more preferably 15% by weight or less, calculated to the total weight of the aqueous composition A.

For attaining the above-mentioned effects, it is preferred that the total concentration of compound(s) according to group a) is in the range of 0.5% to 30% by weight, more preferably in the range of 1% to 25% by weight, still more preferably in the range of 2% to 20% by weight, still further more preferably in the range of 3% to 15% by weight, still further more preferably in the range of 5% to 15% by weight, calculated to the total weight of the aqueous composition A.

Most preferably, from the viewpoint of bleaching performance, the total concentration of mannitol as compound(s) according to group a) is in the range of 0.5% to 30% by weight, more preferably in the range of 1% to 25% by weight, still more preferably in the range of 2% to 20% by weight, still further more preferably in the range of 3% to 15% by weight, still further more preferably in the range of 5% to 15% by weight, calculated to the total weight of the aqueous composition A.

It is further preferred from the viewpoint of cosmetic application that the aqueous composition A comprises water at 30% by weight or more, preferably at 40% by weight or more, more preferably at 50% by weight or more, calculated to the total weight of the aqueous composition A.

It is preferred from the viewpoint of cosmetic safety and hair penetration that the pH of the aqueous composition A is 4 or more, more preferably the pH is 4.5 or more, still more preferably the pH is 5 or more.

It is preferred from the viewpoint of cosmetic safety and hair feel that the pH of the aqueous composition A is 9 or less, more preferably the pH is 8 or less, further more preferably it is 7 or less.

For attaining the above-mentioned effects, it is preferred that the pH of the aqueous composition A is in the range of 4 to 9, more preferably the pH is in the range of 4.5 to 8, further more preferably the pH is in the range of 5 to 7.

For the purpose of the present invention, the pH of the composition is measured by a glass electrode at 25° C. and under atmospheric pressure.

It is further preferred from the viewpoint of user convenience that the aqueous composition A of the present invention is a cleansing composition as defined as above.

Cosmetic Forms of the Aqueous Composition A

In principle, the aqueous composition A may be a solution, a gel, or an emulsion.

It is preferred from the viewpoint of cosmetic applicability that the aqueous composition A comprises one or more surfactant(s) as compound(s) according to d), preferably selected from non-ionic surfactants, anionic surfactants, cationic surfactants, and/or amphoteric/zwitterionic surfactants, and/or their mixtures, more preferably selected from anionic surfactants and/or non-ionic surfactants.

Preferably, the anionic surfactants may be selected from ethoxylated or non-ethoxylated alkyl ether sulfate surfactants, alkyl sulfates, ethoxylated and/or non-ethoxylated alkyl carboxylates, ethoxylated or non-ethoxylated amino acid surfactants, and/or their mixtures.

Suitable examples are alkyl sulfate or preferably ethoxylated alkyl ether sulfate surfactant or mixtures thereof having an alkyl chain length of $C_{10}$ to $C_{22}$.

Suitable non-ionic surfactants may be selected from alkyl polyglycosides, ethoxylated triglycerides, ethoxylated fatty alcohols, ethoxylated fatty acid esters, and/or their mixtures.

Suitable cationic surfactants are quaternary ammonium surfactants having a carbon chain length in the range of $C_{12}$ to $C_{22}$ or surfactants having a tertiary amine group and at least one alkyl chain having a carbon chain length in the range of $C_{12}$ to $C_{22}$ such as alkylamidoalkylamine surfactants. Suitable examples are cetrimonium chloride.

Suitable amphoteric/zwitterionic surfactants are of betaine type. Suitable compounds may be selected from alkyl betaines and/or alkylamido betaines. A preferred compound selected from alkyl betaines is lauryl betaine. A preferred compound selected from alkylamido betaines is cocamidopropyl betaine. The disclosure also relates to the salts of the compounds.

It is preferred from the viewpoint of cleansing power that the total concentration of one or more compound(s) according to d) is 0.1% by weight or more, more preferably it is 0.5% by weight or more, still more preferably it is 1% by weight or more, calculated to the total weight of the aqueous composition A.

It is preferred from the viewpoint of cosmetic safety that the total concentration of one or more compound(s) according to d) is 30% by weight or less, more preferably it is 25% by weight or less, still more preferably it is 20% by weight or less, calculated to the total weight of the aqueous composition A.

For attaining the above-mentioned effects, it is preferred that the total concentration of one or more compound(s) according to d) is in the range of 0.1% to 30% by weight, more preferably in the range of 0.5% to 25% by weight, still more preferably in the range of 1% to 20% by weight, calculated to the total weight of the aqueous composition A.

It is further preferred from the viewpoint of conditioning effect that the aqueous composition A comprises one or more lipophilic compound(s) as compound(s) according to group e).

Suitably, the compound(s) according to group e) is/are selected from $C_{12}$ to $C_{22}$ fatty alcohols, esters of $C_3$ to $C_{12}$ alcohols with $C_{12}$ to $C_{22}$ fatty acids, $C_8$ to $C_{22}$ fatty acids, vegetable oils, and/or silicones, and/or hydrocarbon-based products, and/or their mixtures.

Suitable $C_{12}$ to $C_{22}$ fatty alcohols are myristyl alcohol, cetyl alcohol, stearyl alcohol, behenyl alcohol, and cetearyl alcohol.

Suitable esters of $C_3$ to $C_{22}$ alcohols with $C_{12}$ to $C_{22}$ fatty acids are isopropyl myristate, isopropyl palmitate, and myristyl myristate.

Suitable $C_8$ to $C_{22}$ fatty acids are oleic acid, linoleic acid, and palmitic acid.

Suitable vegetable oils are olive oil, almond oil, sunflower oil, and argan oil.

Suitable silicones are non-aminated and/or aminated silicones. The latter are commonly known as amodimethicones.

Suitable hydrocarbon-based products are mineral oil, paraffins, and Vaseline.

It is preferred from the viewpoint of composition stability that the total concentration of compound(s) according to group e) is 1% by weight or more, more preferably 2% by weight or more, further more preferably 3% by weight or more, calculated to the total weight of the aqueous composition A.

It is preferred from the viewpoint of ease of application that the total concentration of compound(s) according to group e) is 20% by weight or less, more preferably 15% by weight or less, further more preferably 12% by weight or less, calculated to the total weight of the aqueous composition A.

For attaining the above-mentioned effects, it is preferred that the total concentration of compound(s) according to group e) is in the range of 1% to 20% by weight, more preferably in the range of 2% to 15% by weight, further more preferably in the range of 3% to 12% by weight, calculated to the total weight of the aqueous composition A.

Optionally, the aqueous composition A may further comprise one or more thickening agent(s) as defined for composition B below.

The aqueous composition A preferably is a shampoo composition or a hair conditioning composition.

Bleaching Composition B

The kit-of-parts of the present invention also comprises a bleaching composition B comprising b) one or more persalt(s) and/or peroxy salt(s), c) one or more alkalizing agent(s), wherein the bleaching composition B comprises less than 5% by weight of water, calculated to the total weight of the bleaching composition B.

Preferably, the bleaching composition B comprises less than 1% by weight of water, more preferably it is an anhydrous composition, from the viewpoint of stability and maintaining a free-flowing powder. The term anhydrous is to be understood that no water is added to the powder. However, this does not exclude any water bound to the ingredients by, for example, capillary forces.

The bleaching composition A comprises one or more persalt(s) and/or peroxy salt(s) as compound(s) according to group b). Suitable persalts and/or peroxy salts are sodium persulfate, potassium persulfate, ammonium persulfate, earth alkali peroxides such as magnesium peroxide, melamine peroxide or urea peroxide or phthalimidoperoxy hexanoic acid. The preferred persalts from the viewpoint of bleaching power are sodium, potassium, and ammonium persulfate.

It is preferred from the viewpoint of bleaching power and cosmetic safety that the total concentration of persalts and/or peroxy salts in the bleach powder composition is in the range of 10% to 80% by weight, preferably 15% to 70% by weight, more preferably 20% to 60% by weight, and still more preferably 25% to 60% by weight, calculated to the total weight of the bleaching composition B.

The bleaching composition B further comprises one or more alkalizing agent(s) as compounds according to group c). Preferably, the compounds according to group c) are selected from inorganic and/or organic alkalizing agent(s), and/or their mixtures.

It is preferred from the viewpoint of stability and bleaching power that the compounds according to group c) are inorganic alkalizing agent(s), preferably selected from metasilicates, carbonates, and/or bicarbonates, and/or their alkali or earth alkali salts, and/or their mixtures, more preferably the compound according to group c) is sodium metasilicate.

It is preferred from the viewpoint of alkalinity that the compounds according to group c) are organic alkalizing agent(s), preferably selected from alkyl- or alkanolamines according to the general structure

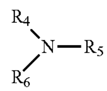

wherein $R_4$, $R_5$, and $R_6$ are same or different H, from $C_1$ to $C_4$, $C_3$ to $C_4$ unsaturated alkyl, $C_3$ to $C_4$ branched alkyl, $C_1$ to $C_4$ hydroxyl alkyl, $C_3$ to $C_4$ unsaturated hydroxyl alkyl, $C_3$ to $C_4$ branched hydroxyl alkyl, with the condition that at least one of $R_4$, $R_5$, or $R_6$ is different from H, and/or their mixtures.

Suitable organic alkalizing agents are monoethanolamine, diethanolamine, triethanolamine, monomethylamine, dimethylamine, trimethylamine, monoethylamine, diethylamine, and 2-aminomethyl propanol.

The most preferred organic alkalizing agent(s) as compounds according to group c) are selected from monoethanolamine and/or 2-aminomethyl propanol.

It is preferred from the viewpoint of alkalinity and stability that the composition comprises one or more compound according to group c) at a total concentration in the range of 0.25% to 30% by weight, preferably 0.5% to 25% by weight, more preferably 1% to 20% by weight, calculated to the total weight of the composition.

Optionally, the bleaching composition may comprise one or more ammonium salt(s) different from persalt(s) and peroxy salt(s).

Suitable ammonium salts different from persalt(s) and peroxy salt(s) are ammonium carbonate, ammonium hydrogen carbonate, ammonium carbamate, ammonium chloride, ammonium sulfate, ammonium phosphates, ammonium nitrate, ammonium bromide, ammonium iodide, ammonium thiosulfate, ammonium molybdate, ammonium vanadate, ammonium sulfamate, ammonium citrate, ammonium salicylate, ammonium valerate, ammonium tartrate, ammonium benzoate, ammonium acetate, ammonium formate and ammonium lactate. Compositions may also comprise mixtures of ammonium salts.

The bleaching composition B may comprise one or more ammonium salts different from persalt(s) and peroxy salt(s) at a total concentration in the range of 0.1% to 10% by weight, calculated to the total weight of the bleaching composition B.

Cosmetic Forms of Bleaching Composition B

The bleaching composition B of the present invention may be in the form of a bleaching powder composition.

For preparation of the bleaching powder composition, an excipient may be added. Such an excipient is diatomaceous earth.

It is further preferred from the viewpoint of cosmetic safety that the bleaching powder composition is dust-free. This property can commonly be achieved by adding lipophilic compounds to the bleaching powder. From this viewpoint, the composition comprises one or more lipophilic compound(s) as compound according to group e).

The bleaching composition B may be in the form of a bleaching paste composition. It is further preferred that the bleaching paste comprises one or more lipophilic compound(s) as compound according to group e).

Suitable compound(s) according to group e) are defined above.

It is preferred from the viewpoint of making the composition dust-free or formulating it as a paste that the concentration of compounds according to group e) is in the range of 1% to 20% by weight, preferably 2% to 15% by weight, more preferably 3% to 12% by weight, calculated to the total weight of the composition.

The bleaching composition B of the present invention may further comprise one or more surfactant(s) as compound according to group d), from the viewpoint of stabilizing the composition and improving wettability and mixability.

Suitable compound(s) according to group d) are defined above.

Suitable concentration ranges for compounds according to group d) in the bleaching composition B are in the range of 0.1% to 10% by weight, calculated to the total weight of the composition.

Optional Compounds—Thickening Polymers

In case the viscosity after mixing with other compositions needs to be further adjusted to prevent dripping, the bleach powder composition may comprise one or more thickening polymers, from the viewpoint of cosmetic safety.

The composition of the present invention comprises one or more thickening polymer(s) selected from non-ionic thickening polymers and/or anionic thickening polymers, and/or their mixtures.

Preferably, the thickening polymers are selected from polymers resulting in an aqueous solution and/or aqueous dispersion at pH between 7 and 12 having a viscosity of at least 1,000 mPa·s measured at a polymer concentration of 1% by weight in water at 25° C., calculated to the total weight of the composition, determined by a Brookfield viscometer, such as at 10 rpm for 1 min, with an appropriate spindle at 25° C.

Suitable non-ionic thickening polymers are cellulose-based polymers. Suitable examples of cellulose-based polymers are methylcellulose, hydroxymethylcellulose, hydroxyethylcellulose, hydroxypropylcellulose, hydroxyethyl-methylcellulose, and alkylated hydroxyl celluloses such as ($C_2$-$C_8$)-alkylcelluloses or cetyl hydroxyethylcellulose.

Suitable anionic thickening polymers are selected from naturally-based anionic polymers and/or synthetic anionic polymers.

Suitably, the natural anionic polymer(s) may be selected from xanthan gum, dehydroxanthan gum, hydroxypropylxanthan gum, carboxymethyl cellulose and starch-based polymers such as vegetable starch and/or their synthetically modified derivatives such as hydroxypropyl starch phosphate. Equally suitable are alginic acids, sodium alginates, ammonium alginates, calcium alginates, gum arabic, and guar gum.

The preferred thickening polymer for the composition of the present invention are natural anionic polymers, more preferably xanthan gum and/or dehydroxanthan gum, from the viewpoint of their biodegradability and low environmental impact.

Preferably, the total concentration of thickening polymers in compositions A, B, and/or C is/are 0.1% by weight or more, more preferably 0.25% by weight or more, more preferably 0.5% by weight or more, calculated to the total weight of each of the compositions A, B, and/or C, from the viewpoint of providing sufficient viscosity to the composition.

Preferably, the total concentration of thickening polymers compositions A, B, and/or C is/are 15% by weight or less, more preferably 12% by weight or more, further more preferably 10% by weight or less, calculated to the total weight of each of the compositions A, B, and/or C, from the viewpoint of providing sufficient viscosity to the composition and cost of goods.

For attaining the above-mentioned effects, it is preferred that the total concentration of thickening polymers compositions A, B, and/or C is/are in the range of 0.1% to 15% by weight, preferably 0.25% to 12% by weight, more preferably in the range of 0.5% to 10% by weight, calculated to the total weight of each of the compositions A, B, and/or C.

Aqueous Oxidizing Composition C

The kit-of-parts of the present invention also comprises an aqueous oxidizing composition C.

The aqueous oxidizing composition C preferably comprises hydrogen peroxide and has a pH in the range of 1 to 6, from the viewpoint of bleaching power and composition stability.

Suitable concentrations of the oxidizing agent(s), preferably hydrogen peroxide, in the aqueous oxidizing composition C is 1% by weight or more, preferably 2% by weight or more, further more preferably 3% by weight or more, calculated to the total weight of the aqueous oxidizing composition C, from the viewpoint of bleaching power.

Suitable concentrations of the oxidizing agent(s), preferably hydrogen peroxide, in the aqueous oxidizing composition C is 20% by weight or less, preferably 15% by weight or less, further more preferably 12% by weight or less, calculated to the total weight of the aqueous oxidizing composition C, from the viewpoint of cosmetic safety.

For attaining the above-mentioned effects, it is preferred that the concentrations of the oxidizing agent(s), preferably hydrogen peroxide, in the aqueous oxidizing composition C is in the range of 1% to 20% by weight, more preferably 2% to 15% by weight, further more preferably 3% to 12% by weight, calculated to the total weight of the aqueous oxidizing composition C.

Suitably, from the viewpoint of cosmetic safety of the aqueous oxidizing composition C, the pH of the composition is 1 or more, preferably the pH is 1.5 or more, more preferably the pH is 2 or more.

Suitably, from the viewpoint of stability of the aqueous oxidizing composition C, the pH of the composition is 6 or less, preferably the pH is 5 or less, more preferably the pH is 4.5 or less.

For attaining the above-mentioned effects, it is preferred that the pH of the aqueous oxidizing composition C is in the range of 1 to 6, more preferably 1.5 to 5, more preferably 2 to 4.5.

The pH may be adjusted with well-known organic or inorganic acids such as phosphoric acid.

Method for Bleaching

The present invention is also directed to a method for bleaching of keratin fibers, preferably human keratin fibers, more preferably human hair, comprising the steps in the following order:

i) applying to keratin fibers an aqueous composition A as defined above,
ii) leaving the keratin fibers for a time period in the range of 1 min to 48 h,
iii) optionally rinsing-off and optionally drying the keratin fibers,
iv) mixing a bleaching composition B with an aqueous oxidizing composition C to yield a ready-to-use composition having a pH in the range of 7 to 12,
v) applying the ready-to-use composition onto keratin fibers and leaving it for a time period in the range of 1 min to 60 min,
vi) rinsing-off the keratin fibers.

It is preferred from the viewpoint of user convenience that the aqueous composition A of step i) is a cleansing composition as defined above.

For this aspect of the present invention, it is preferred from the viewpoint of user convenience that the time period of step ii) is in the range of 1 min to 15 min, preferably in the range of 2 min to 10 min, more preferably in the range of 3 min to 8 min.

It is also preferred from the viewpoint of bleaching power that in step iii) the keratin fibers are dried under hot air flow having a temperature of 45° C. or more.

In another aspect of the present invention, during step ii) the keratin fibers are immersed with the aqueous composition A over the time period of 10 min to 48 h.

In step iv) the bleaching composition B is mixed with the aqueous oxidizing composition C to form a ready-to-use composition. Suitable mixing ratios by weight are 5:1 to 1:5 (bleach powder composition: aqueous oxidizing composition). Customarily, suitable mixing ratios are 1:1, 1:2, and 1:3 by weight (bleaching composition B: aqueous oxidizing composition C).

Suitably, the pH of the ready-to-use composition is in the range of 7 to 12. It is preferred from the viewpoint of accelerated bleaching that the pH of the ready-to-use composition is in the range of 7.5 to 11, more preferably 8.0 to 10.5.

The ready-to-use composition is then applied to keratin fibers and left for a time period of 1 min to 60 min as defined in step v). Preferred time ranges for step v) are 5 min to 45 min, more preferred ranges are 10 min to 35 min, from the viewpoint of sufficiently bleaching the keratin fibers.

After that, the ready-to-use composition is rinsed-off from keratin fibers and optionally they are shampooed and optionally blow-dried.

Use of Aqueous Composition A

The present invention is also directed to the use of an aqueous composition A as defined above as a pre-treatment composition for bleaching of keratin fibers, preferably of human keratin fibers, more preferably of human hair.

Thus, disclosed is a method for bleaching of keratin fibers using an aqueous composition A as defined above as pre-treatment composition prior to the bleaching of keratin fibers.

It is preferred from the viewpoint of user convenience that the aqueous composition A is applied up to 48 h prior to the bleaching treatment.

The following examples are to illustrate the invention, but not to limit it.

Examples

The following aqueous compositions A were prepared.

| Ingredient | Inv. ex. 1 | Comp. ex. 1 |
|---|---|---|
| | % by weight | |
| Mannitol | 5.0 | — |
| Glucose | — | 5.0 |
| NaOH/HCl | Ad pH 5.5 | |
| Water | Ad 100.0 | |
| L* | 39.01 | 36.59 |
| a* | 10.45 | 11.32 |
| b* | 22.95 | 22.04 |
| ΔE | 46.45 | 44.19 |

Bleaching composition B

| | % by weight |
|---|---|
| Hydroxyethylcellulose | 3 |
| Tetrasodium EDTA | 2 |
| Sodium carbonate | 1 |
| Ammonium persulfate | 11 |
| Potassium persulfate | 36 |
| Sodium metasilicate | 10 |
| Mineral oil | 8 |
| Diatomaceous Earth | to 100 |

Aqueous oxidizing composition C

| | % by weight |
|---|---|
| Cetearyl alcohol | 4.0 |
| Sodium lauryl sulfate | 0.8 |
| Phosphoric acid | q.s. ad pH 2.5 |
| Tetrasodium EDTA | 0.05 |
| Hydrogen peroxide | 6.0 |
| Water | ad 100.0 |

Evaluation

The inventive composition comprising mannitol as representative sugar alcohol yielded a higher ΔE in comparison to the composition comprising glucose. This result was unexpected and surprising.

Methods

Bleaching Method

Caucasian hairstreaks (21 cm, 2 g per bundle) were purchased from Fischbach+Miller Haar, Laupheim, Germany. Hairstreaks were placed into the aqueous compositions A from above for 5 min. The hairstreaks were rinsed off with water and then they were blow-dried. The bleaching compositions B from above were mixed in a weight ratio of 1:1.4 (bleaching composition B: aqueous oxidizing composition C) to prepare a ready-to-use composition with a pH of 10.0±0.2. 5 g of the ready-to-use compositions were applied onto hairstreaks and left for 30 min at room temperature. The hairstreaks were then rinsed-off with lukewarm water, shampooed with a shampoo commercially available under the trade name Goldwell Deep Cleansing Shampoo, and blow-dried.

Lightening Measurements

L*, a*, b* values were measured before ($L^*_0$, $a^*_0$, $b^*_0$) and after bleaching ($L^*_1$, $a^*_1$, $b^*_1$) with a Datacolor 45G instrument.

ΔE was calculated by the following equations:

$$\Delta E=\sqrt{(L^*_1-L^*_0)^2+(a^*_1-a^*_0)^2+(b^*_1-b^*_0)^2}$$

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The following examples are within the scope of the present invention.

Example 2

Aqueous composition A

| | % by weight |
|---|---|
| Cocoamidopropyl betaine | 5.0 |
| Sodium laureth sulfate | 8.0 |
| Alkylpolyglycosides | 3.0 |
| Hydroxyethylcellulose | 0.75 |
| Mannitol | 5.0 |
| Lactic acid | ad pH 5.0 |
| Water | ad 100.0 |

The invention claimed is:

1. A kit-of-parts for bleaching keratin fibers comprising:

an aqueous composition A comprising a) at least one non-acetylated sugar alcohol, a bleaching composition B comprising b) a persalt, a peroxy salt, or a combination thereof, and c) at least one alkalizing agent, and an aqueous oxidizing composition C comprising from 1% to 20% by weight of hydrogen peroxide, based on a total weight of the aqueous oxidizing composition C, wherein a total concentration of the least one non-acetylated sugar alcohol a) in the aqueous composition A is from 1% to 30% by weight, based on a total weight of the aqueous composition A, wherein the bleaching composition B comprises less than 5% by weight of water, based on a total weight of the bleaching composition B, wherein the at least one non-acetylated sugar alcohol a) is mannitol, sorbitol, or a combination thereof, wherein the persalt or peroxy salt or a combination thereof b) is ammonium persulfate or sodium persulfate, and wherein the at least one alkalizing agent c) is sodium metasilicate or sodium carbonate.

2. The kit-of-parts according to claim 1, wherein the aqueous composition A comprises at least 30% by weight of water based on the total weight of the aqueous composition A.

3. The kit-of-parts according to claim 1, wherein a pH of the aqueous composition A is from 4 to 9.

4. The kit-of-parts according to claim 1, wherein the at least one non-acetylated sugar alcohol a) is mannitol.

5. The kit-of-parts according to claim 1, wherein the total concentration of the at least one non-acetylated alcohol a) is from 5% to 15% by weight, based on the total weight of the aqueous composition A.

6. The kit-of-parts according to claim 1, wherein the aqueous composition A further comprises d) at least one cleansing surfactant.

7. The kit-of-parts according to claim 6, wherein the at least one cleansing surfactant d) is an anionic surfactant, a non-ionic surfactant, or a combination thereof.

8. The kit-of-parts according to claim 6, wherein the total concentration of the at least one cleansing surfactant d) in the aqueous composition A is from 0.1% to 30% by weight, based on the total weight of the aqueous composition A.

9. The kit-of-parts according to claim 6, wherein the total concentration of the at least one cleansing surfactant d) in the aqueous composition A is from 1% to 20% by weight, based on the total weight of the aqueous composition A.

10. The kit-of-parts according to claim 1, wherein the aqueous composition A further comprises e) at least one lipophilic compound.

11. The kit-of-parts according to claim 1, wherein the aqueous composition A is a shampoo composition.

12. The kit-of-parts according to claim 1, wherein the aqueous composition A is a conditioning composition.

13. The kit-of-parts according to claim 1, wherein the bleaching composition B comprises from 10% to 80% by weight of the compound b) based on the total weight of the bleaching composition B.

14. The kit-of-parts according to claim 1, wherein the persalt or peroxy salt or a combination thereof b) is ammonium persulfate and sodium persulfate, and wherein the at least one alkalizing agent c) is sodium metasilicate and sodium carbonate.

15. The kit-of-parts according to claim 14, wherein the at least one non-acetylated sugar alcohol a) is mannitol.

* * * * *